United States Patent [19]
Pettit

[11] Patent Number: 5,376,798
[45] Date of Patent: Dec. 27, 1994

[54] WEIGHT MEASURING APPARATUS

[75] Inventor: John W. Pettit, Derwood, Md.

[73] Assignee: Adaptive Technologies, Inc., Gaithersburg, Md.

[21] Appl. No.: 990,889

[22] Filed: Dec. 15, 1992

Related U.S. Application Data

[63] Continuation-in-part of Ser. No. 803,796, Dec. 6, 1991, abandoned, which is a continuation of Ser. No. 635,237, Dec. 28, 1990, abandoned, which is a continuation of Ser. No. 341,776, Apr. 21, 1989, Pat. No. 5,099,504, which is a continuation-in-part of Ser. No. 267,646, Nov. 4, 1988, abandoned, which is a continuation of Ser. No. 32,639, Mar. 31, 1987, abandoned.

[51] Int. Cl.$^5$ .................. G01G 9/00; G01N 23/10; H01L 31/117
[52] U.S. Cl. ................ 250/370.14; 250/357.1; 250/359.1
[58] Field of Search ............ 250/357.1, 359.1, 370.14

[56] References Cited
U.S. PATENT DOCUMENTS 3,629,586  12/1971  Giles ........................ 378/56
4,785,186  11/1988  Street et al. ............... 250/370.14

OTHER PUBLICATIONS

C. Bilton, S. Hedges, P. R. Hobson and D. C. Imrie, "Low-cost silicon photodiode for x-ray detection." *J. Phys. E: Sci. Instrum.* vol. 21, No. 8 (Aug. 1988) pp. 809–811.

B. Jurgens, A. Vijftigschild, J. B. Vrijdaghs and H. J. Hopman, "Application of a pin photodiode as a low current electron detector with nanosecond time resolution." *J. Phys. E: Sci. Instrum.* vol. 8 (1975) pp. 629–630.

*Primary Examiner*—Constantine Hannaher
*Attorney, Agent, or Firm*—Dickstein, Shapiro & Morin

[57] ABSTRACT

A low voltage, compact measuring apparatus for measuring the weight of a material is disclosed which uses a PIN diode in conjunction with a low noise processing circuit to detect particle radiation emitted from a source, which source has its detection intensity affected by a material to be measured. A light blocking, particle radiation permeable material protects the PIN diode from detecting light radiation.

11 Claims, 8 Drawing Sheets

GENERAL $$M = Ke + \frac{1}{T}\int e\,dt + D\frac{de}{dt}$$

WEIGHT MEASURING APPARATUS

This application is a continuation-in-part of Ser. No. 803,796, filed Dec. 6, 1991, now abandoned, which is a continuation of Ser. No. 635,237, filed Nov. 28, 1990, now abandoned, which is a continuation of Ser. No. 341,776, filed Apr. 21, 1989, now U.S. Pat. No. 5,099,504, which is a continuation-in-part of Ser. No. 267,646, filed Nov. 4, 1988, now abandoned, which in turn is a continuation of Ser. No. 032,639, filed Mar. 31, 1987, now abandoned.

BACKGROUND OF THE INVENTION

1. Field of the Invention

The present invention relates to a measure weight or presence of material contained in packets or envelopes.

2. Description of Related Art

Scintillation detectors are used as weight measuring sensors but have drawbacks. The scintillation detector uses a material called a scintillator, which, when it absorbs a unit of radiation, becomes activated and will deactivate by giving off light in the ultraviolet range through the process of scintillation. This ultraviolet light is then detected by a quite sensitive light detector known as a photomultiplier tube. The photomultiplier tube is closely coupled to the scintillator material so that ultraviolet light will pass into it. A detection signal from a first photocathode within the photomultiplier tube is typically multiplied by a series of dynode stages which are successively more positive in charge than the preceding dynode stage. The multiplied signal is then taken as an output signal.

A disadvantage of the scintillation detector is that it also uses lethal high voltages in the 1,000 to 3,000 volt range. In addition, the photomultiplier tube characteristics change and drift with use and age and with fluctuations in the high voltage level. This type of a detector is also prone to breakage since it is an evacuated glass tube. Because of its size, weight and cost, this type of detector also cannot be used in many types of environments.

Semiconductor diode particle detectors are also known. They consist of a p-type layer, an n-type layer and an optional intrinsic layer in the middle. This diode is sensitive to light and nuclear and atomic radiation when the same strikes the diode. Detectors of this type have been used for high resolution nuclear spectroscopy. The signal generated by this type of detector consists of the collection of charge released when the radiation loses energy in the sensitive region of the detector. This charge is collected across the p-type and n-type materials and is amplified with a high performance charge sensitive amplifier.

Typically these types of detection devices have a very small output signal. The output signal is so small that noise generated by thermal effects or impurities and imperfections in the silicon material will overcome the charge signal. For this reason, such detectors are typically operated at quite low temperatures, usually through the use of a liquid nitrogen coolant, to arrive at adequate performance. While this type of detector could be used in laboratory research, it cannot be practically used in a production environment.

SUMMARY OF THE INVENTION

In view of the foregoing, it should be apparent that there still exists a need in the art for a reliable, compact, rugged and low cost apparatus and method for measuring weight and the existence of objects. One object of the invention is the provision of a small compact, rugged and low cost-particle radiation detector measuring system which relies on a small and safe radioactive source.

Another object of the invention is the provision of a particle radiation detecting measuring system which operates on low voltages.

A further object of the invention is the provision of a particle detecting apparatus which precisely measures materials through counting particles individually.

Another object of the invention is the provision of a particle detector which is directly compatible with digital computers.

Another object of the invention is the provision of a particle radiation detecting measuring device which can have separable parts. Those parts include a detection head containing those elements necessary for detecting and registering particle counts. A separate part is a processing and display section for monitoring the measurement. A simple low voltage cable passes signals between the two parts.

Still another object of the invention is the provision of a particle radiation detecting weight measuring system for determining the weight of material contained in a packet moving past the particle radiation detecting weight measuring system. Such a system can also be used to provide real-time feedback to the equipment which is used to fill the packets and real-time feed forward to equipment used to direct the conveyance of conforming nonconforming packets.

The present invention makes particular use of a new type of silicon diode detector which contains a p-layer, an n-layer and an intrinsic layer between them and which is operable at room temperature to detect radiation. The device, termed a PIN diode, is primarily intended for detection of laser and ultraviolet light, but it has been discovered that this detector is also sensitive to nuclear and atomic radiation such as beta particles, x-rays and gamma rays.

The invention employs the PIN diode in a particular mechanical and circuit configuration to enhance its ability to detect only particle radiation. A light blocking window is used to screen the PIN diode from the effects of light radiation while the output signal therefrom is connected to a charge sensitive preamplifier. A high quality amplifier is then connected to the output of the preamplifier to develop a suitable signal which can be provided to a threshold detector, the output of which is sent to a pulse rate counter. The output of the pulse rate counter can be used together with pulse rate information derived during previous calibration use of the invention for a packet of known weight to determine a thickness or weight measurement from a detected pulse rate when a packet of unknown weight is provided in the path of the radiation from a source to the PIN diode detector.

Similar calibration and detection steps can be used to employ the invention to determine the presence of an object or weight of material contained in a sealed container.

The PIN diode used in the invention is also preferably surrounded by electrical shielding, which is grounded, preferably to the grounding point of the charge sensitive preamplifier, to minimize spurious signal effects which may affect the relatively low output signal of the PIN diode.

By using the PIN diode and associated small scale electronics packet, a small compact detector can be provided which will allow it to be used in many applications that current weight measuring devices cannot approach. Such a detector can be used in profile extrusion, blown film and blow molding, as well as the typical areas such as sheet and film extrusion. Moreover, since the measurement instrument of the invention requires only low voltage circuits, there is no safety hazard and associated heavily insulated power cables and connections are avoided, thereby opening up new installation possibilities over present day equipment. Still further, the small size and compact solid state construction provide high reliability and stability, while minimizing the possibility of damage from the breakage of glass tubes or gas chambers typically associated with other art devices. Fewer calibration operations and fewer repairs are also attendant with the present construction. Finally, because of it compact size, solid state stage construction and use of relatively low cost components, the detector can be manufactured at lower cost than present generation thickness and weight measurement systems.

Moreover, because of its low cost and compact construction, a plurality of PIN diodes can be arrayed in the vicinity of the packets to be weighed. Because of the complexity and size of present generation equipment, this approach cannot now be achieved, and instead mechanical scanning of a thickness measuring device across the width of a sheet must be employed which has undesired complexity due to the mechanical scanning mechanism. Each of the plurality of thickness or weight measuring devices provided in the array can then be used to control a respective section of processing machinery such as respective lip sections of an extrusion die to control the extruded product to desired specifications or a packet filling device to obtain the desired weight of a filled packet.

By using the PIN diode, the above advantages are obtained for several reasons. First, because the silicon is a solid rather than the gas in the ion chamber, the beta particles will give up energy much faster because of the greater density of a solid than a gas and more collisions will take place with the detector material. This is where the PIN diode gets its efficiency, because nearly all of the beta particles will lose enough energy to be detected in the PIN diode I layer as compared to about 10% to 15% in the gas volume of the ion chamber. Second, when the particles lose energy to the detector, about 30 electron volts of its energy is required to create an ion pair in the ion chamber, whereas about only 0.3 electron volts of its energy are required to create an electron hole pair in silicon. Therefore, a much greater signal will be generated in the PIN diode for a beta particle with a given amount of energy. The signal from the PIN diode is large enough, because of the greater number of electron hole pairs, to be detected over the noise floor by a high speed low noise amplifier and the beta particle can therefore be counted. The ion chamber, on the other hand, cannot generate as large of a signal, so the net ion current produced by a shower of beta particles becomes a DC current that is detected by the ion chamber amplifier.

Because the PIN diode structure is much smaller than the ion chamber, the signal consisting of electron hole pairs can be swept up and collected by lower voltages, (about 30 volts) and in much quicker times (on the order of nanoseconds) than in the ion chamber. This is also responsible for the PIN diode's ability to detect the signal of a single beta particle and count them at high speeds that are required to get a precise measurement in a reasonable period of time for industrial applications.

The above and other objects, advantages and features of the invention will be more readily understood from the following detailed description of the invention which is provided in connection with the accompanying drawings.

DETAILED DESCRIPTION OF THE INVENTION

Figure 1:
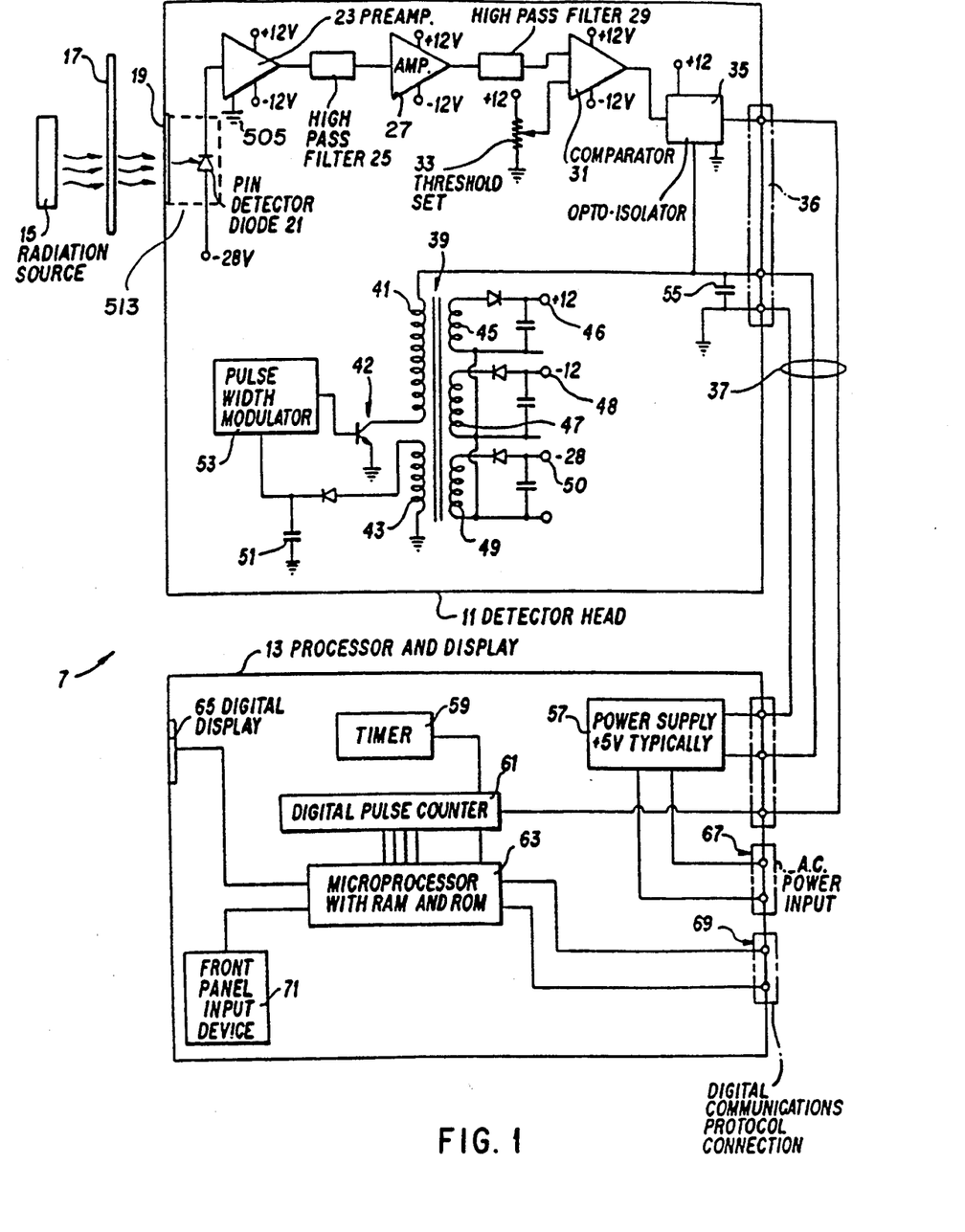
FIG. 1 illustrates in electrical block and schematic form a first embodiment of the present invention.

FIG. 1 illustrates the thickness/density measuring embodiment of the invention in partly schematic, partly block diagram form. The thickness/density measuring system 7 is constructed in two component parts identified in FIG. 1 as the detector head section 11 and processor and the display section 13. These sections are interconnected by a low-voltage cable 37 and are described more fully below.

The detection head section 11 includes the detecting electronics for a thickness/density measurement, while the processor and display section 13 contains the processing and display components for providing a digital display of a thickness/density measurement and/or an output signal representative of the thickness/density measurement which can be used for control purposes.

Turning now to the detector head section 11, it includes a window 19 in the housing which blocks entry of light radiation into the housing, but which permits particle radiation to pass therethrough. Suitable materials which can be used for the window 19 include aluminized mylar. Disposed behind the window 19 and within the housing 11 is a PIN diode 21 which is sensitive to radiation, both light radiation and particle radiation. As noted, the window 19 is impervious to light radiation so that the PIN detector 21 can only detect particle radiation such as x-rays, beta rays and gamma rays. This particle radiation is emitted by the radiation source 15, which is spaced from the window 19. The material 17 to be measured is placed between the radiation source 15 and the window 19.

The output of the PIN diode 21 is connected to a charge sensitive preamplifier 23, the output of which is connected to a first high pass filter 25. The output of the high pass filter 25 is in turn passed to the input of a low noise operational amplifier 27, the output of which then passes through a second high pass filter 29. The output of the high pass filter 29 represents voltage pulses which correspond to charges which are detected by the PIN diode 21. The output of the high pass filter 29 is connected to the input of a comparator 31 which has a threshold set by the resistive network 33 which is applied to another input thereof. The high pass filters block low frequency noise components while the threshold of the comparator 31 is set so that miscellaneous noise which does not constitute a valid detection pulse will not affect the readings of the instrument. When the output of the high pass filter 29 exceeds the set threshold, the comparator 31 provides an output pulse which is then fed to an opto-isolation and line driver circuit 35. The output of the opto-isolation circuit 35 is then connected to a terminal strip on the detector head section 11 for connection with additional processing electronics in the digital processing and display section 13.

Before describing the digital processing and display section 13, the remainder of the circuitry provided in the detector head section 11 will be described.

In order to provide operative power to the various electronic components within the detector head section 11, a power supply is built therein. Because the PIN diode 21 requires different voltages than the other electronic components within the detector head assembly, a multivoltage power supply is provided in the form of a transformer 39 having a plurality of primary windings 41 and 43 and a plurality of secondary windings 45, 47 and 49. The secondary windings are connected to respective diode/capacitor networks and provide the operating D.C. voltages required for the various circuit components within the detector head section 11.

One side of the primary winding 41 is connected to receive an unregulated input voltage applied to an input terminal strip 36 at the detector head section 11 and received from the digital processing and display section 13. This unregulated voltage supply is switched by a transistor switching device 42 under control of a pulse width modulator 53. The pulse width modulator 53 also receives a D.C. voltage input from a primary reference winding 43 through a diode capacitor network 51 such that the pulse width modulator 53, the network 51 and the switching device 42 as well as the primary winding connections function to provide a regulated voltage output at the secondary terminals 46, 48 and 50 of the transformer 39.

An important aspect of the present invention is that the detector head section 11 can be made of very small size and the power supply for the detector head operates on low D.C. voltages, typically less than ±30 volts, which makes the detector head suitable for placement in many environments in which high voltages and/or bulky and complex equipment cannot be provided.

The digital processing and display section 13 provides a low voltage power supply input to the detector head 11 and supplies this via a power supply circuit 57, which receives an A.C. power input 67. Alternatively, a D.C. power source can be provided. The digital processing and display section 13 further includes a timer 59 which defines time windows during which a digital pulse counter 61 is enabled to count pulses which are received from the output of the opto-isolation circuit 35 in the detector head section 11. The pulse counter 61 is gated by the timer 59 to establish a pulse rate counting circuit which provides a count pulse for a given period of time. The output of the digital pulse counter 61 is in turn gated into a microprocessor 63 which includes the usual ROM and RAM memory circuits for storing programs and data. A manually operable panel input device 71, containing a plurality of input switches or keys and input setting devices, is also provided for supplying input information to the microprocessor 63. The microprocessor also provides as output signals a digital signal on terminals 69 representing a thickness, density or weight measurement and an output signal to a digital display 65 provided within the digital processing and display section 13 also representing a thickness, density or weight measurement.

By separating the detector head 11 from the processor and display 13, the size of the detector head can be reduced considerably, as discussed above. Furthermore, if desired, a plurality of detector heads 11 could be multiplexed to a common processor and display 13 to further reduce costs.

At this point, it should be noted that the first embodiment of the invention can be used for a measurement, as explained more fully hereinafter.

The microprocessor 63 contains an algorithm for calculating a weight measurement based on the count rate it receives from the digital pulse counter 61. It is first necessary to calibrate the microprocessor 63 with reference data corresponding to a known weight and a measured count rate for that known weight so that later measurements can be related to this calibration standard. The calibration for and measurement of an unknown thickness of a film will first be described.

Figure 2:
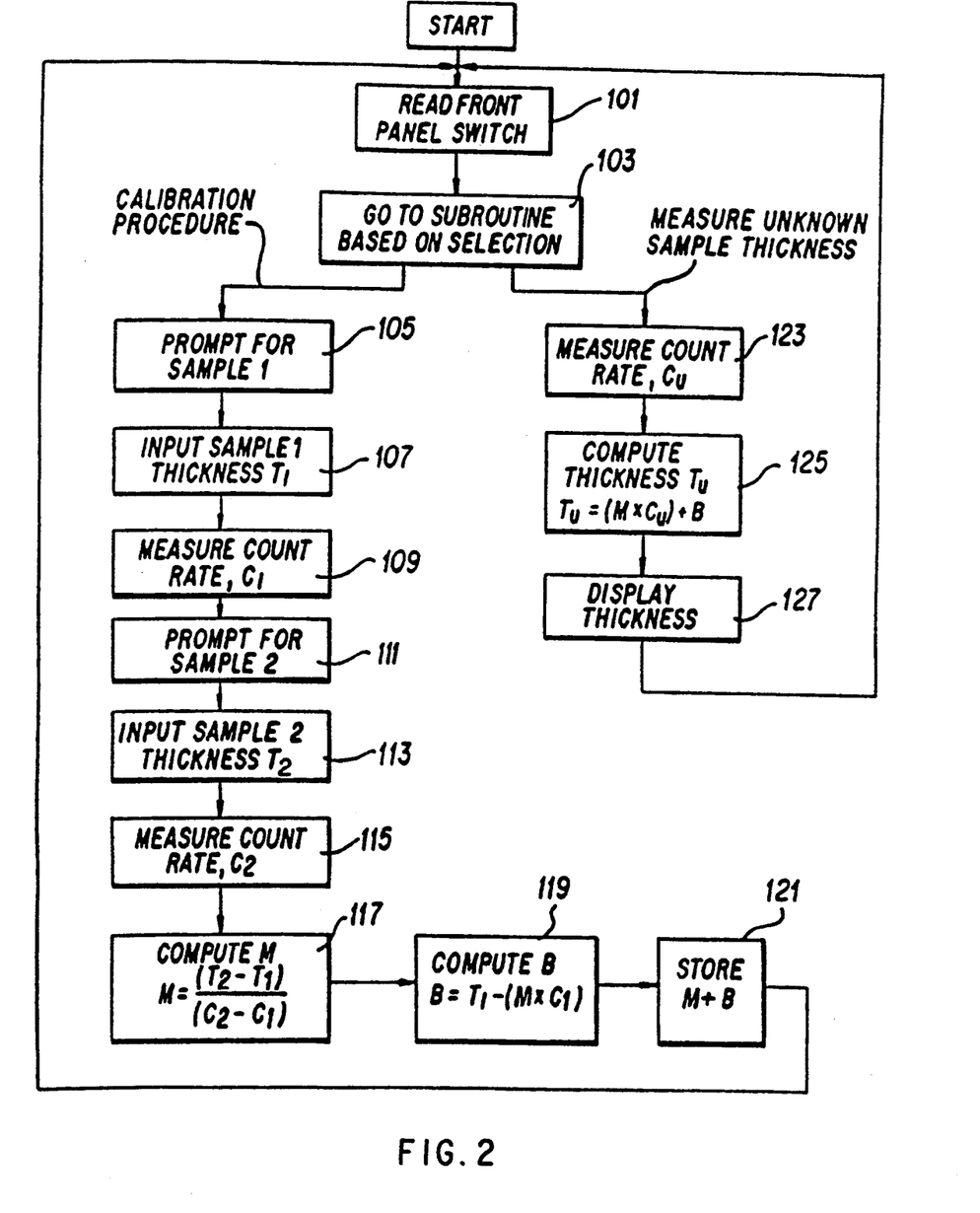
FIG. 2 illustrates in flow chart form a microprocessor program for a method of calibrating and measuring an unknown thickness using the embodiment shown in FIG. 1.

FIG. 2 illustrates in flow chart form the programming of the microprocessor 63 which enables it both to be calibrated in the first instance and then to take thickness measurements thereafter. The operation depicted in FIG. 2 is based on a two sample calibration technique. In a first step 101, a switch on the front panel input device 71 of FIG. 1 is read to determine whether a calibration or a measuring operation is desired. In step 103, the microprocessor determines which type of processing is required. If a calibration procedure is selected by the front panel input device 71, the microprocessor proceeds to step 105 where it displays on the digital display 65 a prompt to an operator instructing him to insert a reference sample into the measuring path between source 15 and the window 19. In addition, the microprocessor further reads a thickness setting input device, e.g., digital value switches, on the front panel input device 71 to obtain a signal representing an actual thickness $T_1$ of this sample. Following step 107, the microprocessor proceeds to step 109 where it measures the count rate $C_1$, for the sample of known thickness in step 109. Following that, the microprocessor activates the digital display 65 to prompt an operator to place a second sample of known thickness between the radiation source 15 and the window 19. In addition, the microprocessor receives an input on the front panel input device 71 of an entered thickness $T_2$ corresponding to the second sample. Thereafter, the microprocessor proceeds to step 115 and measures the count rate $C_2$ for the second sample and after that proceeds to step 117 where it computes a slope M value using the equation $$M = (T_2 - T_1)/(C_2 - C_1) \quad (1)$$

Following that, the microprocessor proceeds to step 119 where it calculates an intercept value B as $$B = T_1 - (M \times C_1) \quad (2)$$

The slope value M and intercept value B are then stored in step 121 for later use by the instrument in calculating the thickness of a sample of unknown thickness.

Returning to step 103, if an actual measurement is desired, the microprocessor proceeds from step 103 to step 123 where it measures a count Cu rate for a sample of unknown thickness. Thereafter it computes an actual thickness $T_u$ using the equation $$T_u = (M \times C_u) + B \quad (3)$$

where M and B are the values previously obtained in the calibration step. This yields a thickness measurement which is then displayed on the digital display 65 in step 127 or alternatively output to control equipment on lines 69 of the digital processing and display unit 13.

Reference is now made to FIGS. 3–10 which represent a further embodiment of the present invention for measuring the weight of filled packets or the presence of a credit, warranty card or other object within an envelope.

Figure 3:
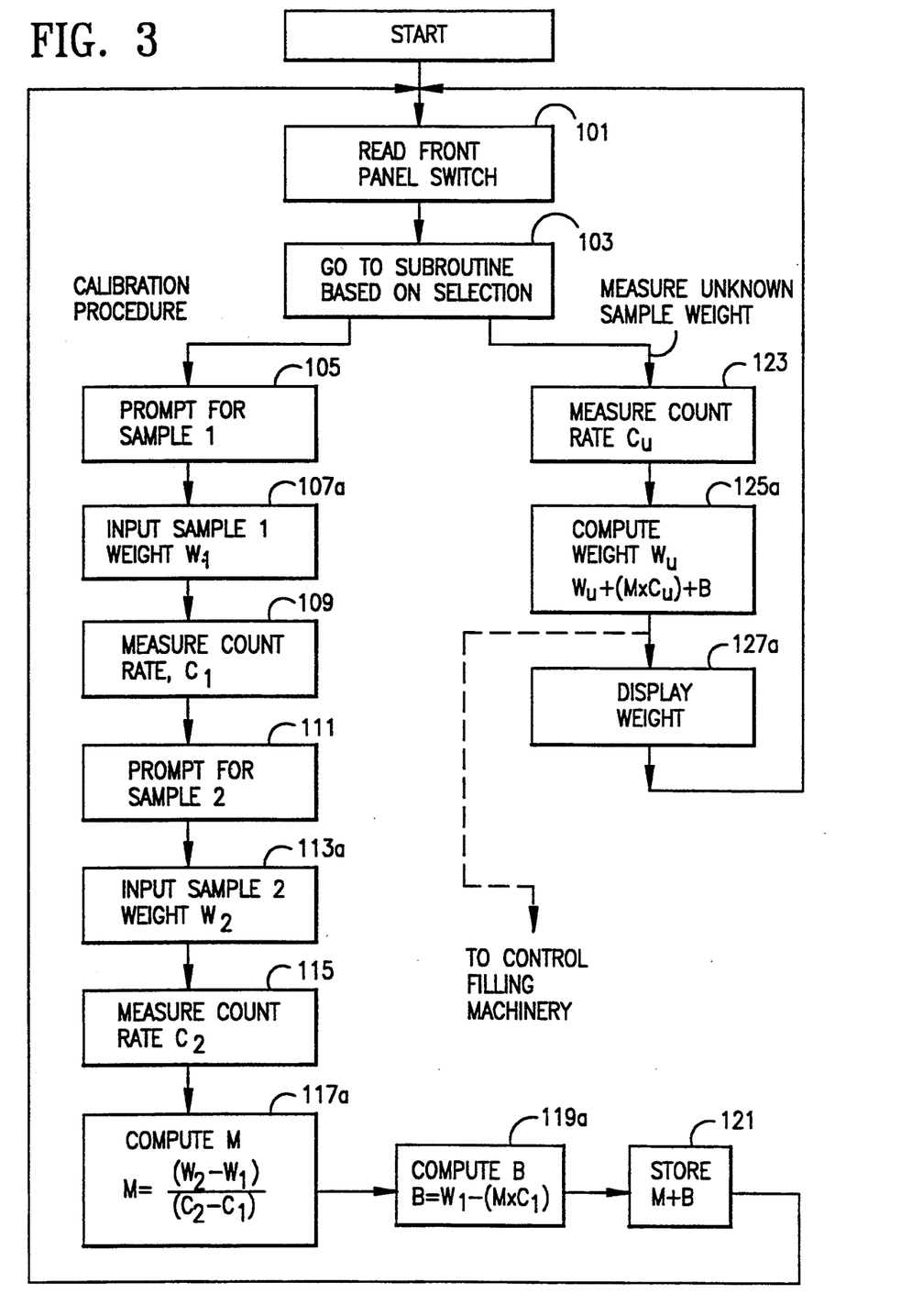
FIG. 3 illustrates in flow chart form a microprocessor program for a method of calibrating and measuring an unknown weight using the embodiment shown in FIG. 1.

Specifically, FIG. 3 shows a modification of the FIG. 2 flow chart to permit the use of the FIG. 1 apparatus for performing a weight measurement and for calibrating the apparatus for such weight measurement. Steps 107, 113, 117, 119, 125 and 127 of FIG. 2 are all modified as new steps 107a, 113a, 117a, 119a, 125a and 127a in FIG. 3. Those new steps are described below without repeating the description of the common steps of FIG. 2 and FIG. 3.

In step 107a, a calibration weight value $W_1$ is entered through the front panel input device for a first sample while in step 113a, a weight value $W_2$ is entered for a second sample. In step 117a, the slope M is computed using the formula $$M = (W_2 - W_1)/(C_2 - C_1) \quad (22)$$

where $C_2$ and $C_1$ represent the respective counts for weights $W_2$ and $W_1$. In step 119a, the intercept B is computed as $$B = W_1 - (M \times C_1) \quad (23)$$

and these values are then stored. The unknown weight measurement ($W_u$) can then be determined in step 125a when the unknown weight measurement subroutine is selected at step 103, as follows $$W_u = (M \times C_u) + B \quad (24)$$

The weight ($W_u$) is then displayed at step 127a.

Output signal produced at step 125a can also be employed in a variety of applications. For example, the weight value can be used to effect feedback/feedforward control the manufacturing process. For example, the output signal from step 125a could be used as a feedback signal to control the speed of a packet filling mechanism (shown in FIG. 5) which fills the packets 1020 (shown in FIG. 4). A feedforward control signal could also be produced to control the sorting of objects whose respective weights exceed preset thresholds. Details of this control example will be elaborated below.

Figure 4:
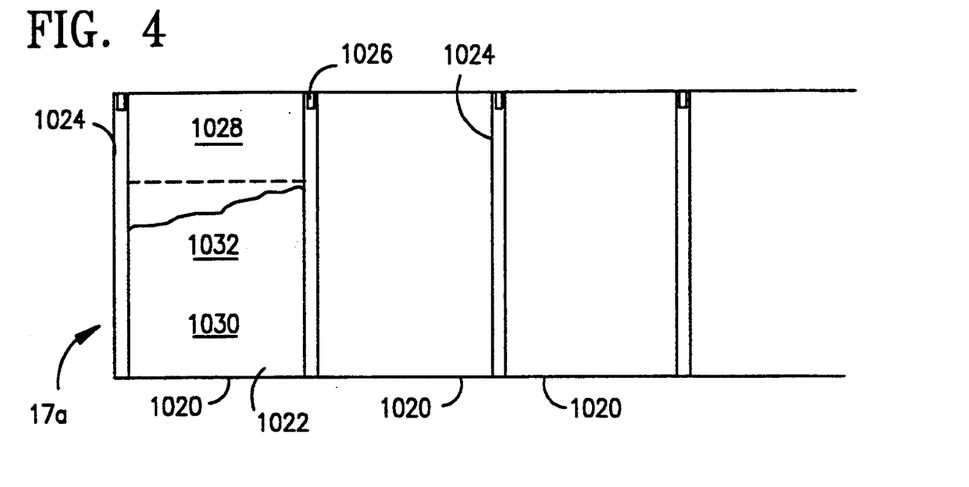
FIG. 4 illustrates in top view a strip of packets containing a particulate material which may be weighed using the flow chart of FIG. 3 in combination with the present invention.

One application of this system relates to the object identified in FIG. 4. This figure is a top-view illustration of a strip of foil packets 17a which are filled with a material 1022 which is to be weighed. It is often important to determine the weight of the material 1022, such as a powder, contained in each of the packets 1020 since certain laws and regulations require that the weight indicated on each of the envelopes or packets 1020 fairly represent the weight of the product 1022 contained in each of those packets 1020. Customers receiving empty or low weight packets may also have problem. Strips of packets 17a, the weight of each of which is to be determined by the instant invention, can be used to contain, for example, lemonade flavored drink mix, or other powdered or particulate material. The packets are formed generally from two separate strips of foil or other type of strip material which are sealed together at seams 1024.

Each packet 1020 is separated from the next packet by the seams 1024. Each seam also contains an identification mark 1026 which can be sensed by a photodetector (FIG. 24) to energize the weight measurement device along with other process steps, such as cutting the strips into individual packets.

In this example, the powder 1022 contained in the packet often has the characteristic of packing in a continuum which can expressed for purposes of visualization as three zones: a "no powder" zone 1028 which is demarcated by the dotted line, a "heavy powder" concentration zone 1030 and a light powder concentration zone 1032.

Figure 5:
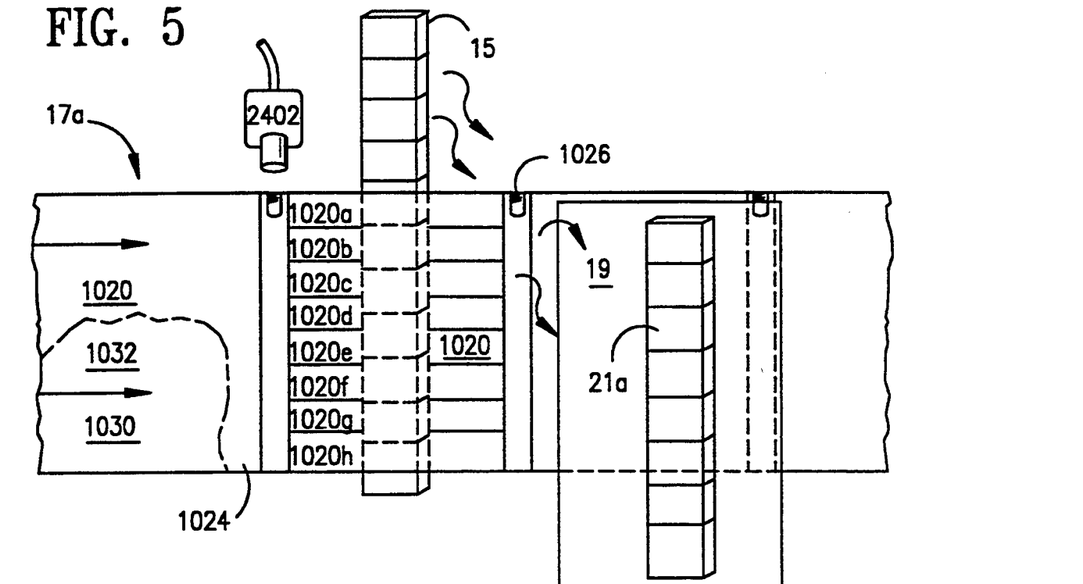
FIG. 5 illustrates in perspective view an alternate embodiment of the radiation source, window and PIN diode detector array, used in connection with the flow chart of FIG. 3 for measuring the weight of material contained in each of the packets shown in FIG. 4.

FIG. 5, illustrates in perspective view the weight detection apparatus. In order to effectively determine packet weight, a PIN diode detector 21a needs to be vertically aligned so that the areas where powder is found, i.e. the light powder and heavy powder zones 1032, 1030 are fully detected.

Strips of packets 17a are passed by the detector 21a in the direction of the arrows from a filling station to a point between the radiation source 15 and the window 19. A PIN diode detector vertical array 21a is located adjacent window 19 so that the radiation that reaches the PIN diode array is representative of the weights of the powder 1022 contained in each of the zones 1030, 1032. In order to effectively measure weight, a uniform curtain of radiation must strike each packet 1020. In prior art systems, this could be accomplished using a line radiation source. However, for the advantages previously discussed, an array of particle sources oriented substantially vertically results in a uniform application of particles across the packet. In the preferred embodiment, a vertical array of eight (8) particle sources and detectors are to match the fill height profile of a packet.

However employed, it is contemplated that any size array can be used.

The vertical array 21a of PIN diodes is disposed opposite the array source 15. Each PIN diode has an active area of one (1) square centimeter which is opposed by its own mating radiation source 15. Operations of the vertical arrays 15, 21a are synchronized with packet conveyance speeds by use of a photodetector 2402 which is oriented, relative to the packets 17a, so that it senses the registration mark 1026 that is located in the seal zone 1024. While a visual indicator and a photodetector combination is illustrated, it is contemplated that any type of mark, such as a magnetic strip, and an associated magnetic detector, could also suffice.

In operation, when the leading edge of the registration mark is detected by the photodetector 2402 counting circuitry associated with the PIN diodes 21a is activated. The distance between the photodetector and particle source is preset so that the beginning edge of the filled area 1020 corresponds to the leading edge of the registration mark 1026.

Timing of the detector initiation also is dependent on the speed of the packet. Specifically, speed is critical for defining the length of time that counters should count to completely scan each packet 1020 without missing the fill material. Thus, if the scan time period is set too short, an incomplete scan may occur. Conversely, if the scan period is set too long, then scanning may run into the seal zone 1024 and provide a deficient weight, or an adjacent filled packet 1020, and provide an excessive weight measurement.

Many techniques exist for timing packet weight detection. For example, the conveyor speed can be synchronized with the detector and a motor controller timer to time detector activation/deactivation. Another example of detector initiation is based on the observation of the count pattern that causes an initiation of the weight detector. In other words, the particle count signature itself can be used as a means to auto-synchronize the PIN diode detectors.

Typically, as the packet passes by the detector array, the count rate will dramatically increase after scanning the fill area 1020 when the seal zone 1024 passes by the detector. A count threshold value change is used to signify that the next fill area 1020 has entered the detection area. Similarly, when the fill area 1020 passes by the detector 21a, a lower count is produced due to the adsorption of particles by the fill material. Thus, when the particle count increases, the particle counters can be stopped since the count signifies that the fill area 1020 has exited the detection area. The timer can be calibrated at the initiation of processing.

In order to determine weight, each PIN diode observes a given number of counts for each packet 1020 as it passes by the detector array. The count from each detector 21a can then be sent to a computer for conversion into the weight of a horizontal strip 1020a–1020h of the packet scanned by that particular PIN diode. After the conversion, the horizontal strips 1020a–1020h can be added together to obtain the total weight of the packet. The conversion algorithm can be the same previously described by formulas 22–24. However, other known weight conversion formulas can also be applied.

By processing the counts from each PIN diode, non-linearities due to non-uniform fill profiles of the powder in each packet 1020 are avoided. However, a disadvantage of this arrangement is that individual processing results for each diode must be separately accumulated and then transmitted at the particular timed moment. Consequently, a relatively expensive processor would need to be utilized. An alternative arrangement is to electronically combine the outputs of all PIN diodes in a single count, or any division of that count. The resulting count can then be converted into a weight measurement. An example of a single count circuit arrangement 2500 for two PIN diodes is shown in FIG. 6.

Figure 6:
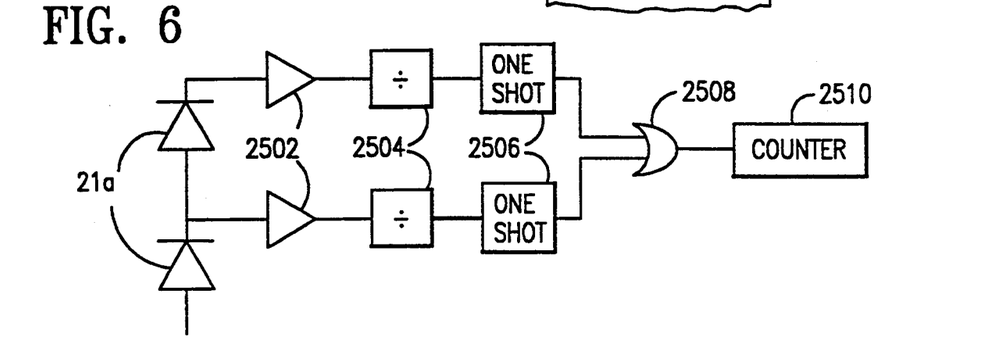
FIG. 6 illustrates in electrical block and schematic form an example of the divider circuit shown in FIG. 24.

Specifically, FIG. 6 illustrates a pulse combining circuit 2500 which is connected to a pair of the PIN diodes 21a. The output of each diode is respectively fed to a comparator 2502. Each comparator 2502 is in turn connected at its respective output to a four-bit divider circuit. The divider circuit output is then fed to a one-shot or monostable multi-vibrator 2506 the output of which is a respective leg of an OR gate 2508. The OR gate output feeds the particle counter 2510.

Although a pair of PIN diodes 21a are shown as the inputs to the divider circuit 2500, it is contemplated that any number of PIN diodes can be combined in one divider circuit 2500. Using the circuit arrangement shown in FIG. 25, therefore, a total of four dividers would be employed with the PIN diode array 21a.

In operation, the comparator 2502 filters the PIN diode output to remove spurious signals. The four-bit dividers 2504 divide the outputs from the PIN diode comparator so that the count rate seen by each leg of the OR gate 2508 is reduced. The purpose of the divider is to avoid the problem of having pulses from the PIN diode pair overlap at the OR gate 2508. The disadvantage of overlap is that when the pulses arrive at the same time, the OR gate's output to the counter is the same as when only a single pulse is present. A miscount thus occurs. Moreover, miscounts are a common problem in most detection applications for the PIN diode array since pulses from the PIN diodes are generated independently of one another, and are produced at high rates.

To further reduce the probability of overlap, the outputs of the four-bit dividers 2504 are fed to the one-shot multi-vibrators 2506 to produce a pulses of short duration for pulses sent from the PIN diode pair. Each multivibrator reduces the pulse width from 1 ms. to between 20–50 ns. As a consequence, the chance of pulse overlap is greatly reduced at the OR gate 2508.

Figure 7:
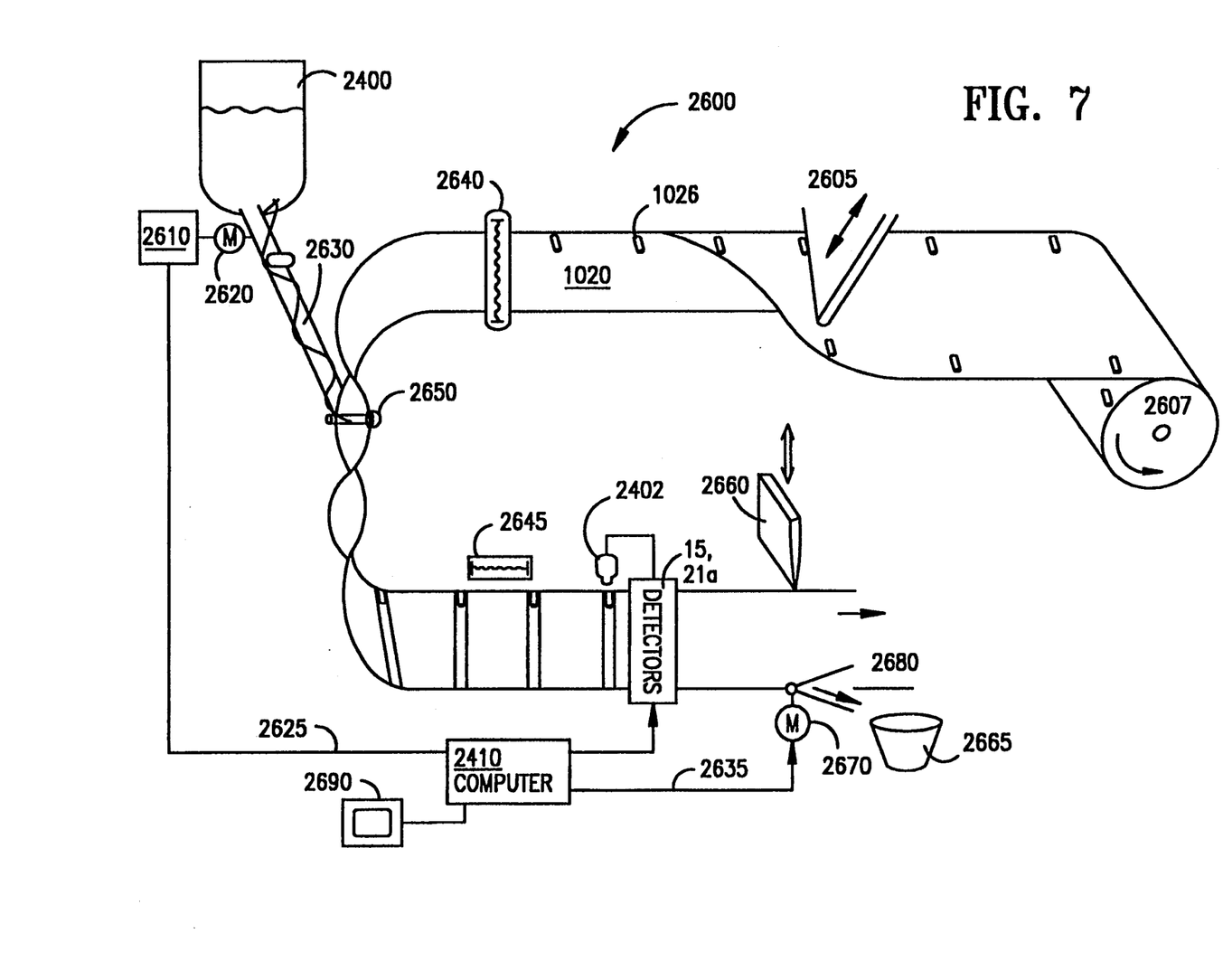
FIG. 7 is a schematic view of a packet manufacturing assembly line employing the precut invention shown in FIGS. 22–25.

Referring now to FIG. 7, a schematic illustration of an application of the present invention in a packet filling assembly 2600 is illustrated. Specifically, the exemplified process involves the creation of a strip of individual packets 1020, as illustrated in FIG. 4 and the filling, sealing, weighing and sorting of those packets. This assembly is known as form, fill and seal ("FFS").

FFS utilizes a roll of packet stock foil 2607 which is mounted in close proximity to a conveyor device. The FFS contains appropriate apparatus to unroll the stock foil in the conveying direction indicated by the arrow. As the material is unrolled, individual packets are folded together by action of the packet folding anvil 2605 that is adapted to reciprocate over the conveyed packets in order to fold the material in half.

The folded packets 1020 are then conveyed under heater 2640. The heater consists of a cartridge heat seal device which pulses the packets 1020 when the registration mark 1026 is sensed by an appropriate sensing device (not shown). Once heating is completed, the packet contains three sealed sides and an open top.

The packets are then conveyed to a location between a pair of suction devices 2650. When activated, the suction devices open the unsealed top of each packet at a point beneath an auger outlet 2630 connected to a feed hopper 2400 that contains powder for filling each packet 1020. The auger motor 2620 is then activated to fill the packet with the powder contained in vat 2400.

While activation of the auger motor may be controlled by sensors associated with suction devices 2650, motor speed, which controls the rate at which material flows into each packet 1020 is controlled, in part, by a feedback control signal provided from the detector arrays 15 and 21a located downstream from the auger 2630. The feedback control signal will be described in further detail below.

Filled packets are then conveyed to a second heater 2645 which heat seals the open top of each packet 1020. The packets are aligned with a photodetector 2402 or other appropriate sensor so that on sensing the leading edge of the registration mark 1026, the detectors 15, 21a are activated. The weight detectors then send the weight signal, as previously described, to a computer control display 2410 and 2690. A feedback signal is then sent to the motor control 2625 in the event that the control weight is found to vary from weight thresholds set in the computer. Thus, if the packet is found to be too light, a feedback signal is sent to motor control 2610 to speed up motor 2620 and thus cause the auger to feed powder at a faster rate. Alternatively, if detector 15/21a determines that the packets contain too much powder, then the feedback control signal will cause motor 2622 to slow down.

If the detected weight in each packet significantly varies from a set threshold, a feedforward signal is also sent by computer 2410 to a reject mechanism, such as a motor 2670 for opening and closing a diverter. A delay to accommodate the transit time needed for the packet to enter the sort mechanism after exiting the detector 15, 21a is also implemented in the feedforward control software. The motor in turn opens and closes a diverter 2680 so that packets containing an inappropriate weight of material can be diverted and discarded 2665. Hence, feedforward control is provided by the present invention in order to control sorting of underweight or overweight packets at the FFS process. The instant invention described in this example thereby provides real-time control at high speeds and with accurate results.

Figure 8A:
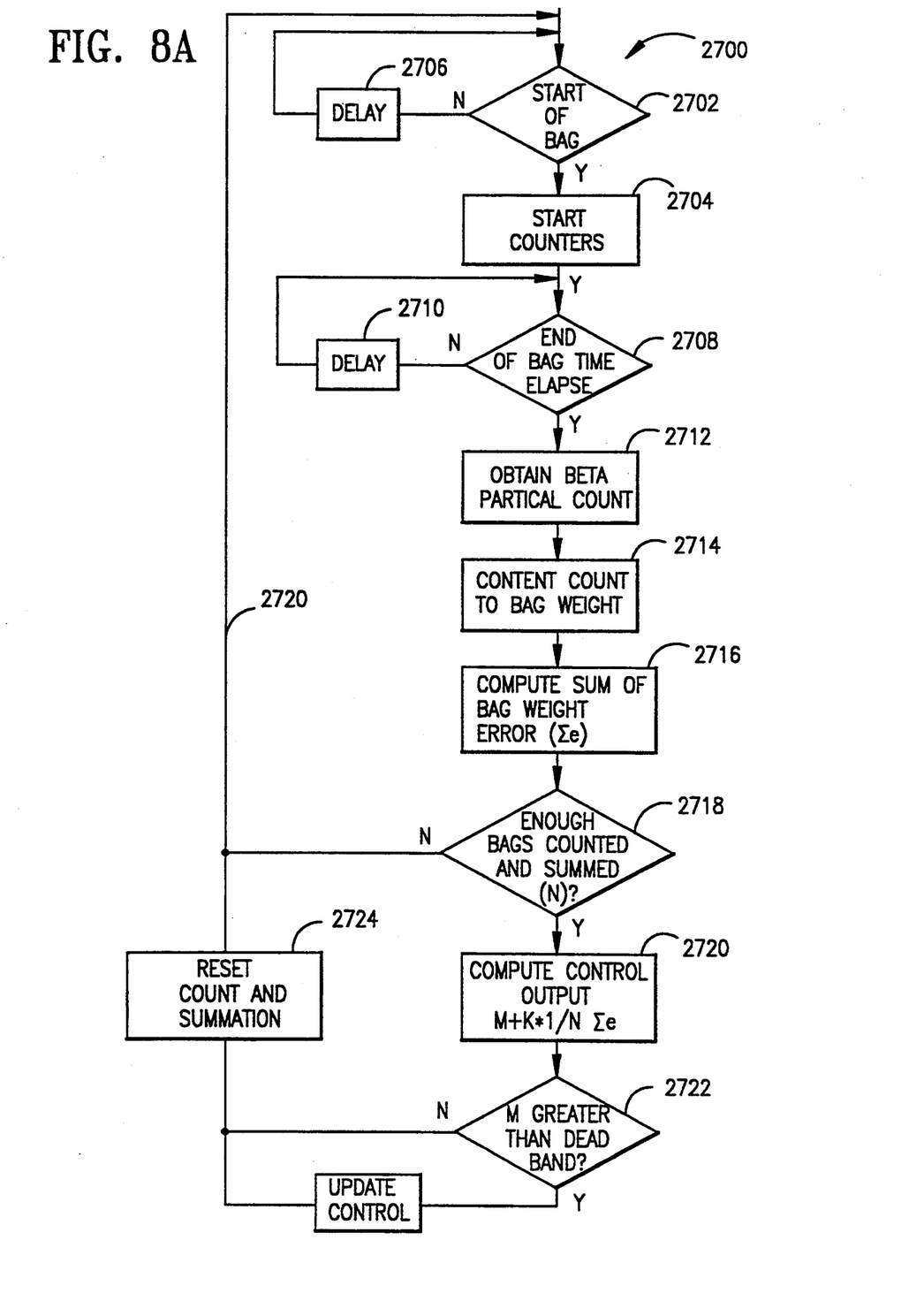
FIGS. 8A and 8B illustrate in flow chart form the packet weight initial setups for effecting feedback control to the packet filling device shown in FIGS. 5 and 7.

FIG. 8A is a flow chart illustrating the control algorithm employed by the exemplified invention shown in FIG. 7.

The control process 2700 is initiated by testing for a registration mark 1026 for each packet 1020. If the registration mark is sensed at step 2702, then the detector counters 21a are activated at step 2704. Otherwise, the registration mark detector continues to test for presence/absence of the mark after a brief delay 2706.

If the detectors are activated at step 2704, then the PIN diodes count particles until a significant increase in the particle count is detected which signifies that the seal 1024 has been reached at step 2708. Alternatively, a preset time period can be set marking the time it would take for each packet to traverse the detector array 21a. If the end of packet has not timed-out at step 2710, then after a brief delay, an end of packet condition is tested again. Otherwise, the counters are stopped at step 2712 and the detector 21a provides the computer 2410 with the beta count produced from detector array 21a. The count is then converted to a packet weight value at step 2714 in accordance with the previously described technique (see flow chart in FIG. 3). The sum of the packet weight error is then computed at step 2716. The error e is based upon a comparison of the threshold packet weight and the actual detected packet weight. The packet weight error sum e is then stored for later processing. A counter also keeps track of the number of packets counted N.

For meaningful results, the number of packets detected N must be counted and summed in order that the error value e is a reliable indicator of an incorrect auger speed. For high volume FFS systems an optimal value for N is between 50 and 100 packets. However, any number of packets can be used. If enough packets were not counted in step 2718, therefore, then processing loops back at 2720 to test for the next packet. Otherwise, the control output is produced by the computer at step 2720. The control output value M is defined by the formula illustrated in step 2720. The value K is a proportionality factor representing speed control. In other words, K represents how much change in the speed for the auger motor 2620 is necessary to effect a given change in packet weight. The proportionality factor is experimentally determined to yield best control results. The control function is based on the product of the proportionality factor and the average error for each packet counted.

Once the control value M is determined, then the value is tested at step 2722 to see whether it exceeds a dead band value. Dead band represents a value range for acceptable packet weight variations. The dead band is included to eliminate constant feedback adjustments due to small variations in packet weight that cannot be optimally controlled. The dead band is typically set to be about 0.5 to 2.0 times the standard deviation of the packet weight distribution, depending on how responsive and tight the operator desires the weight control function to be.

If M does not exceed a dead band i.e. the packet weight has not drifted out of the dead band range, then the control output has not changed and the packet count and weight values are reset at step 2724. Otherwise, the value M is updated at step 2726 and its value, along with the initialized count and summation values, are provided respectively to the motor controller and to the computer 2410.

Figure 8B:
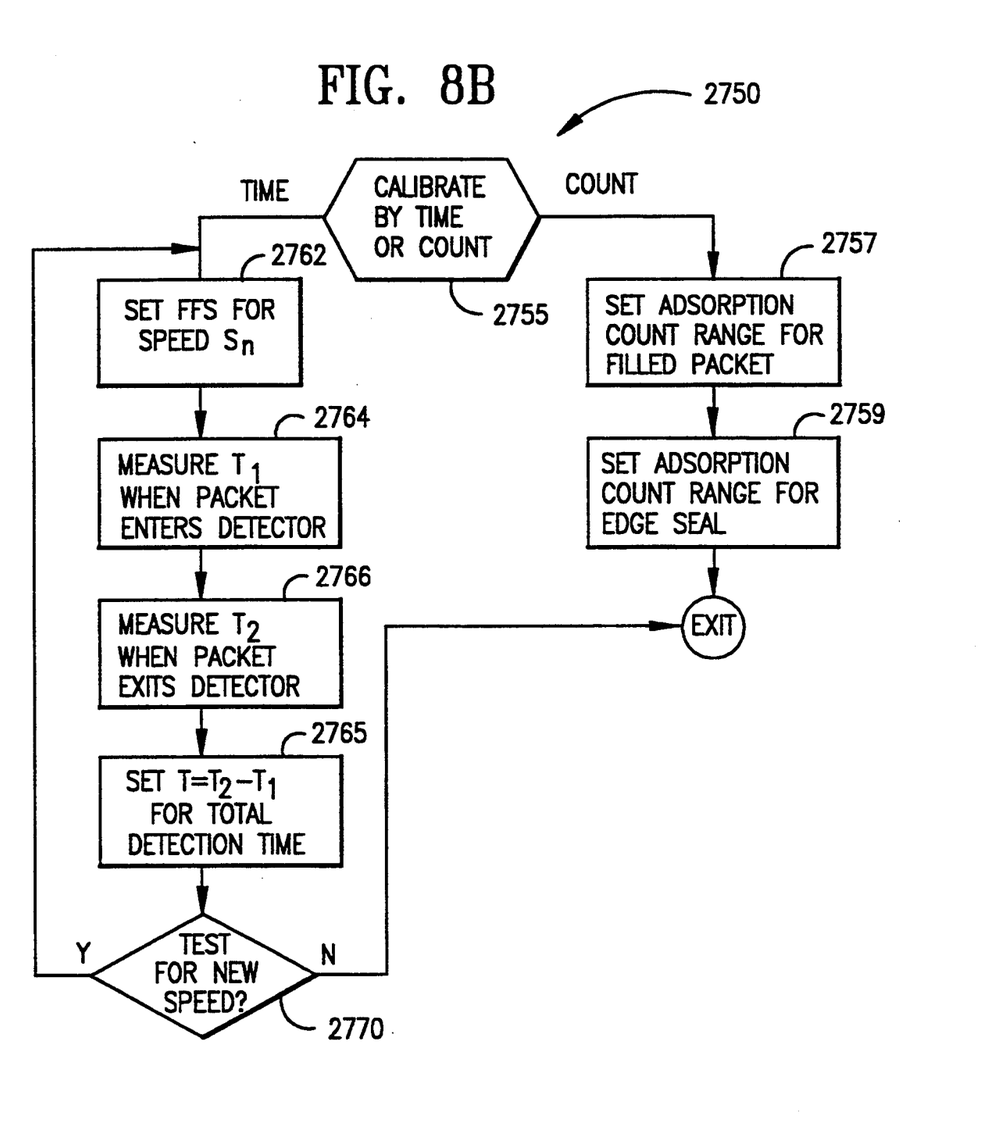

FIG. 8B is the calibration routine that sets up the detector particle count period to coincide with the traversal time that the packet 1020 is present in the detector 15, 21a. The routine 2750 opens with a menu which enables an operator to either calibrate the detection period based on time or on count, as previously discussed. If particle count is chosen, then the operator is asked to provide a range of count values that are acceptable for indicating the presence of a powder-filled packet, at step 2757. The operator then sets a range of count values that represent the adsorption values at the edge seal 1024 of the packet 1020 (step 2759). If the time calibration choice is initiated, the operator first indicates the particular speed setting for the FFS as value $S_n$. An entry time value $T_1$ is then set to indicate the time point in which the packet 1020 enters the detector 15, 21a. At speed $S_n$ the packet traverses the detector until the edge seal 1024 crosses the detector. At this point the end time $T_2$ is set. The total traverse time at speed $S_n$ is then set at step 2768. The operator is finally queried whether he wants to calibrate traversal time for another speed setting at step 2770.

Figure 9:
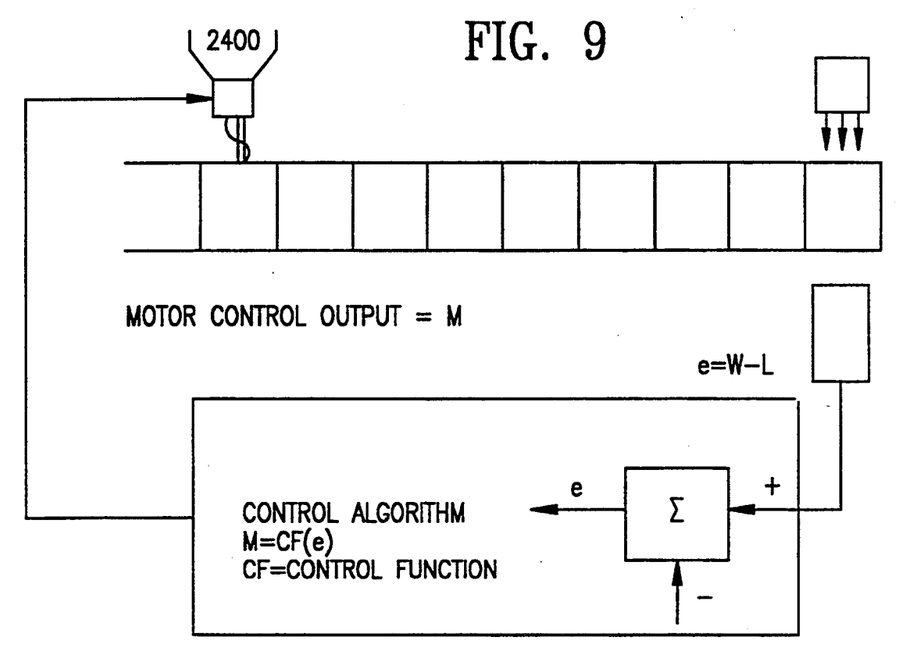
FIG. 9 illustrates in block form the packet weight control functions implemented by the control computer shown in FIGS. 5 and 7.

Referring now to FIG. 9, a block diagram of the computer control algorithm for feedback control of the auger motor is shown. This functional block diagram illustrates a PID control scheme for perfecting the conveying speed control for filling the packets. The formula, as illustrated, produces a motor control output M to control the auger motor speed. The desired packet weight value is entered by the operator. K represents the proportional gain previously described while T is an integration time constant and D is a derivative time constant. K, T and D are also adjusted values for optimum control. A dead band value B can also be compared to the absolute value of M such that if the absolute value M is less than D, then M is set to zero (no change in motor speed). Otherwise, if the absolute value of M exceeds B then the updated motor control value is transmitted to the motor controller 2610.

As a result of the process, variations in packet weight is minimized so that conditions, such as density of powder in the hopper, auger speed fluctuations, or assembly line conveying speed variations can be readily controlled with minimal effect on the quality of product produced. The control system as exemplified above lowers the production set point to a value that is much closer to the declared weight value on the packet label—which must be met or exceeded by law. The result is thereby a dramatic savings in powder costs which improves production profitability. A more consistent and higher quality product also is produced.

Figure 10:
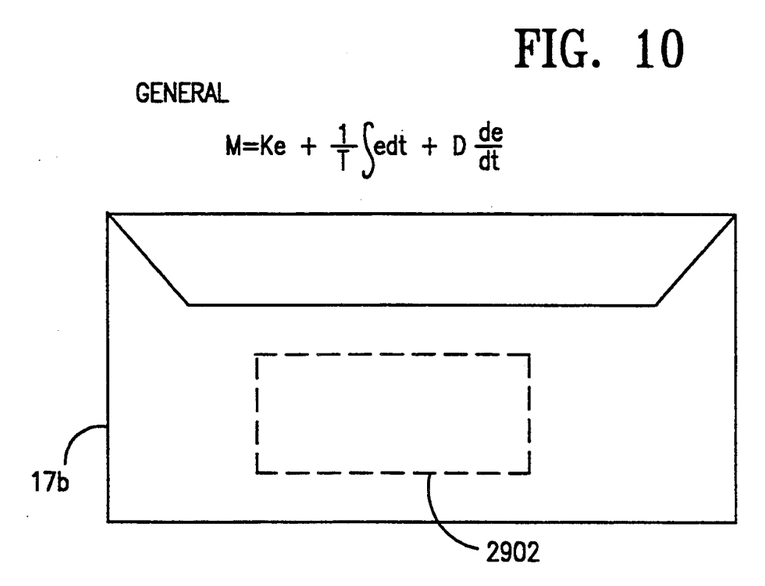
FIG. 10 is a top view illustration of an envelope containing an object the presence of which may be detected using the flow chart of FIG. 3 and the alternate embodiment of the radiation source and PIN detector diode array of FIG. 5.

The embodiment of the present invention shown in FIGS. 3–9 can also be used to determine the absence or presence of a guaranty card or credit card 2902 as shown in FIG. 10. In an envelope 17b. Each of the envelopes 17b can be passed either singly between the radiation source 15 and the window 19 or can be passed on some type of carrier material between the radiation source 15 and the window 19. Each of the envelopes 17b would be temporarily secured to that carrier material.

In all of the embodiments of measurement systems described above, whether thickness, density, denier or weight, it should be recognized that the measured value may be displayed and/or used as a controlling signal to other processing devices.

While various embodiments of the present invention have been described and illustrated in connection with the drawings, it should be apparent that many modifications can be made to the invention as described, without departing from the spirit and scope of the invention. Accordingly, the invention is not limited by the foregoing description but is only limited by the scope of the claims appended hereto.

What is claimed is:

1. A weight measuring apparatus for measuring the weight of material contained in each one of a moving strip of continuous packets, each one of said packets integral with at least one adjacent of said packets, comprising:
    a particle radiation source;
    a particle radiation detector array formed from a plurality of PIN diodes arranged in a matrix, said particle radiation detector array spaced apart from said particle radiation source and each of said PIN diodes in said array producing first output signals representative of the weight of material contained in one of said packets;
    means for preventing light radiation from striking said PIN diode array but permitting particle radiation from said particle radiation source to strike said PIN diode array; and
    circuitry for receiving said first output signals from said PIN diodes in said array and for calculating a second output signal representative of the weight of the material contained in one of said integral strips of adjacent packets.

2. The weight measuring apparatus of claim 1, further including means for filling each of said packets with said material and a control system for controlling said filling means utilizing said second output signal such that a correct weight of said material is placed in each of said packets.

3. The weight measuring apparatus of claim 1, wherein said material contained in each of said packets is a granular material.

4. The weight measuring apparatus of claim 1, further including a charge sensitive preamplifier connected to an output of each of said PIN diodes in said array;
    an amplifier coupled to the output of each preamplifier;
    a comparator coupled to the output of each amplifier and providing a third output signal when the level of the output of said amplifier exceeds a set threshold; and
    means responsive to the third output signals of each comparator for providing said second output signal representative of the weight of the material contained in a packet which was placed in a position to affect the radiation from said particle radiation which reaches said PIN diode array.

5. The apparatus of claim 1, wherein said PIN diodes of said particle radiation detector array are vertically spaced from one another and are arranged transverse to a direction of movement of said strip of packets, said PIN diodes spaced so as to match a fill height profile of each of said packets.

6. A method for determining the weight of material in each one of a plurality of packets formed into a continuous strip of such packets, each one of said packets integral with at least one adjacent of said packets, comprising the steps of:
    processing said strip of packets containing said material past a source of particle radiation;
    irradiating said strip of packets with particle radiation from said source of particle radiation;
    preventing light radiation from striking a plurality of PIN diode detectors while permitting said particle radiation irradiating said strip of packets to strike said plurality of PIN diode detectors;
    sensing said particle radiation which passes through the material in each of said packets in said strip of packets using said plurality of PIN diode detectors; and
    computing the weight of each one of said plurality of packets using output signals generated by said plurality of PIN diode detectors that represent the weight of material in each one of said packets.

7. A weight measuring apparatus for measuring the weight of material contained in each one of a moving strip of packets, each one of said packets integral with at least one adjacent of said packets, comprising;
    a particle radiation source that directs particles at said moving strip of packets;
    particle radiation detection means having PIN diodes for measuring, on a packet-by-packet basis, particles from said moving strip of packets indicative of the weight of material contained in each of said packets; and means for determining the weight of material contained in each one of said packets in accordance with said particles measured by said particle radiation detection means.

8. The apparatus of claim 7, wherein said PIN diodes of said particle radiation detection means are vertically spaced from one another and are arranged transverse to a direction of movement of said strip of packets, said PIN diodes spaced so as to match a fill height profile of each of said packets.

9. The apparatus of claim 7, further comprising means for preventing light radiation from striking said PIN diodes.

10. A weight measuring apparatus for measuring the weight of material contained in each one of a strip of continuous packets, each one of said packets integral with at least one adjacent of said packets, comprising:
a particle radiation source; a particle radiation detector array formed from a plurality of PIN diodes arranged in a matrix, said particle radiation detector array instantaneously measuring radiation particles from one of said packets, representative of the weight of material contained in said one of said packets, as said strip of packets and said particle radiation detector array are moved relative to each other;
means for preventing light radiation from striking said particle radiation detector array; and
a processor for calculating the weight of material in said one of said packets in response to said corresponding measured radiation particles.

11. The apparatus of claim 10, wherein said PIN diodes of said particle radiation detector array are vertically spaced from one another and are arranged transverse to a direction of movement of said strip of packets, said PIN diodes spaced so as to match a fill height profile of each of said packets.

* * * * *